United States Patent [19]

Simon

[11] Patent Number: 4,783,284

[45] Date of Patent: Nov. 8, 1988

[54] PROCESS FOR THE PREPARATION OF ALKYL-5,6,7,8-TETRAHYDROANTHRAHYDROQUINONES

[75] Inventor: Dietolf Simon, Bad Hönningen, Fed. Rep. of Germany

[73] Assignee: Peroxid-Chemie GmbH, Hoellriegelskreuth, Fed. Rep. of Germany

[21] Appl. No.: 907,898

[22] Filed: Sep. 16, 1986

[30] Foreign Application Priority Data

Sep. 24, 1985 [DE] Fed. Rep. of Germany ....... 3534014

[51] Int. Cl.$^4$ .............................................. C07C 50/18
[52] U.S. Cl. ..................................................... 260/369
[58] Field of Search ......................................... 260/369

[56] References Cited

U.S. PATENT DOCUMENTS 3,432,267 3/1969 Lee et al. ............................ 260/369
3,888,890 6/1975 Kirchner et al. ................... 260/369

FOREIGN PATENT DOCUMENTS 537685 3/1957 Canada ................................ 260/369

OTHER PUBLICATIONS

*Chemical Abstract*, vol. 95, #203,235q, 1981, Li et al., "Poly(vinypyrrolidone)–palladium (II) Complex as homogenous and heterogenous hydrogenation catalyst for alkenes.
*Chemical Abstract* vol. 93#, 150,853q 1980, Perchenko (I) et al., "Study of the Catalytic Properties of Polyethyleneimine Coordination Compounds".
*Chemical Abstract*, vol. 100, #67870k, 1983, Perchenko et al., (II), Catalytic Conversion of 1,3 cyclohexadiene in the presence of Polyethyleneimine Complex with Metal Catalysts.

*Primary Examiner*—Richard L. Raymond
*Assistant Examiner*—Raymond Covington
*Attorney, Agent, or Firm*—Felfe & Lynch

[57] ABSTRACT

The present invention provides a process for the preparation of alkyl-5,6,7,8-tetrahydroanthrahydroquinones, wherein an alkylanthraquinone is hydrogenated with a catalyst which consists of an organic polymer to which a metal of the noble metal or platinum metal group is bound coordinatively or covalently.

16 Claims, No Drawings

PROCESS FOR THE PREPARATION OF ALKYL-5,6,7,8-TETRAHYDROANTHRAHYDROQUINONES

The present invention is concerned with a process for the preparation of alkyl-5,6,7,8-tetrahydroanthrahydroquinones.

It is known to use alkylanthraquinones in admixture with the hydrogenation-stabilised alkyltetrahydroanthraquinones for the production of hydrogen peroxide by the anthraquinone process. The tetrahydroanthraquinones thereby automatically result in the process cycle as hydrogenated by-products of the alkylanthraquinones. However, hitherto it was not possible to prepare alkyltetrahydroanthraquinones with a simple process. Therefore it would be desirable to prepare the tetrahydro derivatives in a separate synthesis under optimum hydrogenation conditions and to use them directly in the anthraquinone process.

It is an object of the present invention to provide a process with which alkylanthraquinones can be hydrogenated in high yield to the tetrahydro derivatives and, on the other hand, to avoid the known disadvantages of the hydrogenation usually carried out heterogenocatalytically, such as adsorption/desorptions problems, non-uniformity of the product formation by inhomogeneity of the catalytic centres of reaction.

Thus, according to the present invention, there is provided a process for the preparation of alkyl-5,6,7,8-tetrahydroanthrahydroquinones, wherein an alkylantraquinone is hydrogenated with a catalyst which consists of an organic polymer to which a metal of the noble metal or platinum metal group is bound coordinatively or covalently.

This process is very simple to carry out and yields the tetrahydro derivatives in the hydroquinone form in a highly selective manner. Subsequent oxidation of the tetrahydroanthrahydroquinones with an oxygen-containing gas gives, in known manner, the corresponding tetrahydroanthrahydoquinones. However, it is especially advantageous to introduce the tetrahydroanthrahydoquinones as such directly into the anthraquinone process in the course of the process of which they are then reacted to give tetrahydroanthrahydoquinone and hydrogen peroxide.

In carrying out the process according to the present invention, the alkylanthraquinone to be hydrogenated is either dissolved in a solvent dissolving all of the components, especially in an alcohol containing up to 10 carbon atoms and preferably up to 4 carbon atoms, or in a cyclic or acyclic acid amide or in a water-immiscible solvent system. In the latter case, the catalyst is placed into the aqueous solution; the hydrogenation then takes place in the emulsified two-phase system of aqueous catalyst solution and organic alkylanthraquinone solution.

Examples of solvents which can be used include alcohols, especially those containing up to 10 carbon atoms, such as methanol, ethanol, propanol, isopropanol, butanol, tert.-butanol, isobutanol and diisobutyl carbinol, hydrogenation-stable ketones, such as diisobutyl keytone, cyclohexanone, aromatic, alicyclic and/or aliphatic hydrocarbons and the alkoxy and halogen derivatives thereof, such as, in particular, alkylated or alkoyxlated benzenes or naphthalenes and/or cyclic or acyclic acid amides or tetra-substituted ureas, such as tetramethylurea. Especially preferred are alcohols with up to 4 carbon atoms or acid amides, such as N-methylpyrrolidone and dimethylformamide, for the homogeneous mixing and mixture of diisobutyl carbinol with alkyl-aromatics for the heterogenous method of working with emulsion formation (aqueous catalyst solution).

The hydrogenation takes place with a catalyst present in aqueous or organic solution. The catalyst consists of an organic polymer to which a metal of the noble metal or platinum metal group is coordinatively bound. Such a catalyst can be produced, for example, by mixing an aqueous solution of the organic polymer with the appropriate metal salt and then, by passing in hydrogen, the metal is precipitated on to the carrier in molecular form. As metal salt, there is used, for example, the corresponding chloride.

Organic polymers are used as carrier materials. Preferred polymers include polyvinylpyrrolidone, polyethyleneimine, carboxymethylcellulose, polyvinyl alcohol, polyvinylamine and/or amylose. These polymers can also be present in substituted form. Thus, for example, polyethyleneimine can be substituted on the nitrogen by reaction with chloroacetic acid. Polyvinylpyrrolidone is especially preferred. Also especially preferred as organic polymeric carriers for the catalyst are polymers with a molecular weight of more than 100,000 and preferably of more than 300,000. After conclusion of the hydrogenation reaction, these high molecular weight polymers can then easily be separated off by ultrafiltration.

The catalytically active metals which are coordinatively bound to the polymer originate from the noble metal or platinum metal group. As catalytically active metals, there are preferred rhodium, ruthenium, palladium, osmium, iridium and/or platinum and more preferably rhodium and/or palladium. Rhodium which is bound to polyvinylpyrrolidone is especially preferably used as catalyst.

The hydrogenation of the alkylanthraquinones takes place either in the two-phase system formed from the water-immiscible solvent system and the aqueous solution (emulsion hydrogenation) or in a homogeneous one-phase system. The heterogeneous system has the advantage of being easy to work up by separating the phases, whereas in the homogeneous system, better catalyst life times are achieved.

The concentration of the catalyst is preferably in the range of from $10^{-2}$ to $10^{-4}$ g. atom of metal per liter of hydrogenation solution. Especially preferably, the metal bound to the polymer is used in an amount of from $10^{-3}$ to $10^{-4}$ g. atom of metal per liter of hydrogenation solution.

In the case of the process according to the present invention, for the hydrogenation the organic polymer is preferably loaded with an amount of from 0.5 to 10% by weight, referred to the polymer, of the metal. Especially preferably, the metal loading is from 1 to 6% by weight, referred to the polymer.

As alkylanthraquinones which are hydrogenated, there are preferably used anthraquinones which are alkylated in the 2-position. Especially preferably, anthraquinones are hydrogenated which are substituted in the 2-position with a $C_1$ to $C_{10}$ alkyl radical and especially with an ethyl, tert.-butyl or amyl radical.

The process according to the present invention can be carried out without increasing the pressure and at ambient temperature. However, the hydrogenation is preferably carried out at a pressure of from 0.5 to 5 MPa and especially preferably at 1 to 4 MPa and at a temperature of from 20° to 70° C.

The hydrogenation is carried out especially preferably at a hydrogen pressure of from 1.5 to 2.5 MPa. At this pressure, the relationship of yield, height of pressure and speed of the reaction is the most favourable. The temperature of the hydrogenation step is especially preferably in the range of from 40° to 60° C.

In a preferred embodiment of the process according to the present invention, in the case of which a catalyst based on PVP is used as hydrogenation catalyst, the speed of the hydrogenation reaction is also influenced by catalytic amounts of acid. The addition of a small amount of acid results in an increase of the speed of reaction. The addition of, for example, 0.1 ml. sulphuric acid per liter of solution is sufficient.

When the reaction is concluded, the hydrogenated product, the alkyl-tetrahydroanthrahydroquinone, is separated from the reaction mixture. In the case of emulsion hydrogenation, the aqueous catalyst solution is first separated, which can take place by simple decantation and possibly subsequent centrifuging. The separation of the tetrahydroanthrahydroquinone from the organic solvent can, as desired, take place by crystallisation in the cold or by concentration of the solution or by the addition of a precipitation agent.

If hydrogenation is carried out in a homogeneous phase system, the catalyst is preferably separated off by ultrafiltration or by extraction and the product is then obtained by concentration of the filtered or extracted solution, preferably in a vacuum, and crystallisation from the concentrate.

For carrying out the process according to the present invention, the catalyst is dissolved in the chosen organic or aqueous solvent and this solution is then treated for several hours with hydrogen at normal pressure and ambient temperature, a dark coloration being obtained. In the case of working in a homogeneous phase, the anthraquinone is then added to the thus activated catalyst solution and dissolved with warming. When a catalyst based on polyvinylpyrrolidone is used, a catalytic amount of acid is preferably added and the reaction mixture obtained is hydrogenated in a stirrer autoclave. In the case of working in a heterogenous phase, after the activation, the solution of the alkylanthraquinone in an organic solvent system is added to the aqueous catalyst solution with hydrogen and the further hydrogenation is carried out, possibly with the addition of catalytic amounts of acid, in the autoclave with intensive stirring. In the case of an emulsion hydrogenation, the phases separate after ending the stirring and can easily be decanted off. The separated organic phase is preferably further centrifuged in order to remove emulsified residues of catalyst solution as quantitatively as possible.

The catalyst production itself can take place, for example, by mixing the chosen polymer, for example polyvinylpyrrolidone (PVP), in aqueous or alcoholic solution with the appropriate noble metal salt, for example the chloride of the noble metal in question and then, by passing in hydrogen, the metal is precipitated on to the carrier in molecular form.

The process according to the present invention is characterised by high yields which are practically quantitative. Very many hydrogenation cycles are possible without the catalyst activity decreasing markedly. Due to the high selectivity, which almost achieves 100%, the formation of by-products, which could contaminate the end product, is kept to a minimum.

The following Examples are given for the purpose of illustrating the present invention:

EXAMPLE 1

A 2-alkylanthraquinone, the composition of which is given in the following Table 1, was hydrogenated in a homogeneous phase with catalysts based on polyvinylpyrrolidone. The hydrogenations took place after the addition of 0.4 ml. concentrated sulphuric acid per liter of solution with variation of the catalyst metal, metal content, quinone, quinone concentration, temperature, pressure, solvent and period of reaction. The following Table 1 gives a survey of the results obtained.

TABLE 1

| Expt. No. | catalyst metal+ Type | content g Atom Metal/l. | Alkylanthraquinone Alkyl radical | content mol/l | Temperature °C. | pressure MPa | solvent | period h | hydrogenation conversion++ in % |
|---|---|---|---|---|---|---|---|---|---|
| 1 | Rh | 29.2 × 10⁻⁴ | Amyl | 6.8 × 10⁻² | 50 | 1 | Ethanol | 2 | 65 |
| 2 | Rh | " | Amyl | " | " | " | " | 4 | 94 |
| 3 | " | " | " | " | " | 2,5 | " | " | 100 |
| 4 | " | " | " | " | " | 1 | Butanol | 2 | 51 |
| 5 | " | " | " | " | " | " | " | 4 | 92 |
| 6 | Pd | " | " | " | " | 0,5 | Ethanol | " | 65 |
| 7 | " | " | " | " | " | 1 | " | " | 94 |
| 8 | " | " | " | " | " | 2,5 | " | " | 100 |
| 9 | Rh | 6.5 × 10⁻⁴ | Ethyl | 28.0 × 10⁻² | 40 | 2,0 | N—Methylpyrrolidone | " | 31 |
| 10 | " | 13.0 × 10⁻⁴ | " | " | 60 | " | " | " | 66 |
| 11 | " | 6.5 × 10⁻⁴ | " | " | 40 | " | Dimethylformamide | " | 25 |
| 12 | " | 13.0 × 10⁻⁴ | " | " | 60 | " | " | " | 49 |

+metal loading of the polymer:
6% by wt. experiments 1-8
1% by wt. experiments 9-12
++referred to amount of alkylanthraquinone used

EXAMPLE 2

The selectivity of the hydrogenation process according to the present invention was investigated using the example of the homogeneous reaction with rhodium-polyvinylpyrrolidone in butanol as solvent. Hydrogenation was carried out with a catalyst metal content of $29.2 \times 10^{-4}$ g. atom of metal/liter of hydrogenation solution, the metal loading of the polymer being 6% by weight in all cases. The alkylanthraquinone content was $60.5 \times 10^{-3}$ mole/liter solution. The hydrogenation took place after the addition of 0.4 ml. concentrated sulphuric acid to 1 liter of hydrogenation mixture. The following Table 2 gives the yields obtained in the case of practically complete hydrogenation reaction of the alkylanthraquinone under different reaction conditions.

TABLE 2

| expt. No. | alkyl radical/ anthraquinone | pressure MPa | temperature °C | period h. | yield of tetrahydroanthraquinone derivative in % |
|---|---|---|---|---|---|
| 1 | tert.-butyl | 1 | 50 | 4 | 91.0 |
| 2 | " | 1 | 50 | 6 | 98.5 |
| 3 | " | 1 | 50 | 8 | 98.0 |
| 4 | " | 2.1 | 60 | 1.5 | 98.0 |
| 5 | " | 2.1 | 60 | 3.5 | 98.7 |
| 6 | ethyl | 2.5 | 50 | 2 | 97.4 |
| 7 | " | 2.5 | 50 | 4 | 98.2 |

It can be seen that this hydrogenation system is very stable. After 6 hydrogenation cycles in succession with the same catalyst sample, there was no loss of activity of the catalyst.

EXAMPLE 3

Hydrogenation in heterogenous phase

With the use of Rh/PVP dissolved in 150 ml. water and of 2-amylanthraquinone ($24 \times 10^{-2}$ mole/liter) dissolved in the organic solvents given in the following Table 3, a hydrogenation was carried out in emulsified phase at 50° C. for 4 hours. 0.4 ml. concentrated sulphuric acid was added as activator. The following Table 3 gives the hydrogenation results obtained under different reaction conditions.

TABLE 3

| expt. No. | % metal loading/ polymer | Rh content+ g.atom/l. | solvent for the alkylanthraquinone | pressure MPa | hydrogenation reaction in % |
|---|---|---|---|---|---|
| 1 | 6 | $4.9 \times 10^{-3}$ | diisobutyl-carbinol/C 10 aromatic mixture | 4.0 | 100 |
| 2 | 1 | $4.9 \times 10^{-3}$ | diisobutyl-carbinol/C 10 aromatic mixture | 2.5 | 85 |
| 3 | 1 | $1.9 \times 10^{-3}$ | cyclohexanone | 2.5 | 68 |
| 4 | 1 | $1.9 \times 10^{-3}$ | tetraline | 2.5 | 19 |
| 5 | 1 | $1.9 \times 10^{-3}$ | $CCl_2F-CCl_2F$ | 2.5 | 13 |

+content per liter of aqueous catalyst solution.

I claim:

1. A process for the preparation of an alkyl-5,6,7,8-tetrahydroanthrahydroquinone, comprising hydrogenating an alkylanthraquinone with a catalyst which consists of an organic polymer to which a metal of the noble metal or platinum group is bound coordinately or covalently and wherein said polymer-bound metal is present in a dissolved form.

2. The process of claim 1, wherein a 2-alkylanthraquinone is hydrogenated.

3. The process of claim 1 wherein the anthraquinone is dissolved in an alcohol, hydrogenation-stable ketone, aromatic, alicyclic and/or aliphatic hydrocarbon or an alkoxy or halogen derivative thereof or a cyclic or acyclic acid amide and/or a tetrasubstituted urea compound.

4. The process of claim 3, wherein hydrogenation is carried out in a homogeneous phase in an alcohol containing up to 10 carbon atoms and/or an acid amide.

5. The process of claim 3, wherein the hydrogenation is carried out in a heterogeneous phase with an emulsion of an aqueous catalyst solution and of an alkylanthraquinone solution in an organic, water-immiscible solvent or solvent mixture.

6. The process of claim 1, wherein the organic polymer is polyvinylpyrrolidone, polyethyleneimine, carboxymethylcellulose, polyvinyl alcohol, polyvinylamine and/or amylose and/or a derivative of these polymers.

7. The process of claim 1, wherein the metal is ruthenium, rhodium, palladium, osmium, iridium and/or platinum.

8. The process of claim 6 wherein the catalyst is rhodium or palladium bound to polyvinylpyrrolidone.

9. The process of claim 2 wherein hydrogenation is carried out with a concentration of polymer-bound metal of from $10^{-2}$ to $10^{-4}$ g. atom of metal per liter of solution.

10. The process of claim 1 wherein the metal loading on the polymer is from 0.5 to 10% by weight, referred to the polymer.

11. The process of claim 1 wherein hydrogenation is carried out at a hydrogen pressure of from 0.5 to 5 MPa.

12. The process of claim 11 wherein the hydrogenation is carried out at a temperature of from 20° to 70° C.

13. The process of claim 1 wherein the polymer comprises polyvinylpyrrolidone and the catalyst additionally comprises a catalytic amount of acid.

14. The process of claim 1 further comprising separating the alkyl-5,6,7,8-tetrahydroanthrahydroquinone by the crystallisation, ultrafiltration, phase decantation or extraction.

15. A process of claim 1 wherein
   the organic polymer is polyvinylpyrrolidone, polyethyleneimine, carboxymethylcellulose, polyvinyl alcohol, polyvinylamine and/or amylase and/or a derivative of these polymers;
   the metal is ruthenium, rhodium, palladium, osmium, irridum and/or platinum,
   the metal loading on the polymer is 0.5 to 10% by weight referred to the polymer weight;
   the hydrogenation is carried out with hydrogen at a pressure of 0.5 to 5 MPa and a temperature of 20° to 70° C.

16. The process of claim 15 wherein the catalyst is rhodium or palladium bound to polyvinylpyrrolidone.

* * * * *

UNITED STATES PATENT AND TRADEMARK OFFICE
CERTIFICATE OF CORRECTION

PATENT NO. : 4,783,284
DATED : November 8, 1988
INVENTOR(S) : Dietolf Simon

It is certified that error appears in the above-identified patent and that said Letters Patent is hereby corrected as shown below:

Col. 1, line 33:     change "alkylantraquinone" to
                      -- alkylanthraquinone --.

Col. 1, line 63:     change "keytone" to -- ketone --.

Col. 6, line 48
   and
New Claim 15, line 7: change "irridum" to -- iridium --.

Signed and Sealed this

Twenty-seventh Day of June, 1989

Attest:

DONALD J. QUIGG

*Attesting Officer*            *Commissioner of Patents and Trademarks*